United States Patent
Skaliter et al.

(10) Patent No.: US 6,403,316 B1
(45) Date of Patent: Jun. 11, 2002

(54) ISOLATION OF CDNA ENCODING FOR SECRETED OR MEMBRANAL PROTEINS

(75) Inventors: Rami Skaliter; Paz Einat, both of Ness-Ziona; Orna Mor, Kiryat Ono; Lion Novak, Tel-Aviv, all of (IL)

(73) Assignee: Quark Biotech, Inc., Ness-Ziona (IL)

( * ) Notice: Subject to any disclaimer, the term of this patent is extended or adjusted under 35 U.S.C. 154(b) by 0 days.

(21) Appl. No.: 09/534,661

(22) Filed: Mar. 24, 2000

Related U.S. Application Data

(60) Provisional application No. 60/125,975, filed on Mar. 24, 1999.

(51) Int. Cl.[7] .................... C12Q 1/68; C12P 19/34; C12M 1/36; G01N 33/53
(52) U.S. Cl. .................... 435/6; 435/7.2; 435/91.1; 435/287.2
(58) Field of Search ............... 435/6, 91.1, 287.2, 435/7.2

(56) References Cited

U.S. PATENT DOCUMENTS

| | | | |
|---|---|---|---|
| 4,483,920 A | * | 11/1984 | Gillespie et al. ............ 435/6 |
| 6,013,437 A | * | 1/2000 | Luria et al. ................ 435/6 |

OTHER PUBLICATIONS

Walker et al. Techniques in Molecular Biology, 1983, pp. 120–127.*
Lewin, B. Genes V, Oxford University Press, 1994, pp. 281–282.*
Mechler, B.M. "Isolation of Messenger RNA from Membrane–Bound Polysomes" Methods in Enzymology, 1987, 152:241–248.*

* cited by examiner

Primary Examiner—W. Gary Jones
Assistant Examiner—B J Forman
(74) Attorney, Agent, or Firm—John P. White; Cooper & Dunham LLP

(57) ABSTRACT

The present invention provides a method of identifying clones encoding for membranal and secreted proteins by deriving probes from membrane-bound polysomes and free-polysomes, and performing a microarray-based comparison of the relative abundance of the different RNA species. Analysis of the results of such comparison and resultant identification of clones encoding for membranal or secreted proteins, provides an efficient tool for identifying targets of drug development. The present invention further provides a method of augmenting a microarray analysis by utilizing RNA extracted from specific subcellular compartments as templates for DNA probes. The method may be used together with conventional differential analysis techniques for improvement of their analysis and gene identification functions.

5 Claims, 3 Drawing Sheets

ISOLATION OF CDNA ENCODING FOR SECRETED OR MEMBRANAL PROTEINS

CROSS REFERENCE TO RELATED APPLICATIONS

This is a conversion of U.S. Provisional Patent Application No. 60/125,975, filed Mar. 24, 1999, incorporated herein by reference.

BACKGROUND OF THE INVENTION

1. Field of the Invention

The present invention relates to the identification of cDNAs and genes encoding secreted or membranal coding mRNAs. More specifically, the present invention relates to a method of identifying clones encoding for membranal and secreted proteins by deriving probes from template RNA extracted from membrane-bound polysomes and free polysomes and performing microarray-based comparison of the relative abundance of different RNA species. Analysis of the results of such comparison and identification thereby of clones encoding for membranal or secreted proteins provides a valuable tool which may be used together with other gene discovery tools, and which in itself enables identification of likely targets for drug development.

2. Description of Related Art

The discovery of novel genes and the elucidation of their role in normal and pathological processes is a major goal of biomedical research. Gene expression profiling with cDNA microarrays is currently widely used to obtain broad information on expression patterns of thousands of genes in conjunction with various biological conditions (Spellman et al., 1998; Iyer et al., 1999; Feng et al., 1999; Wang et al., 1999; Whitney et al., 1999). Schena et al. developed a high capacity system to monitor the expression of many genes in parallel utilizing microarrays. The microarrays are prepared by high speed robotic printing of cDNAs on glass providing quantitative expression measurements of the corresponding genes (Schena et al., 1995). Differential expression measurements of genes are made by means of simultaneous, two color fluorescence hybridization. Other methods that may be used for differential expression measurement are, for example, Affymetrix, oligochip, SAGE, differential display and its variants and subtractive hybridization.

Powerful bioinformatics tools have been developed in order to classify and identify interesting genes according to their gene expression profiles (Eisen et al,m 1998; Bassett et al., 1999) and associate them with a condition of interest. The identification and/or isolation of genes whose expression differs between two cell or tissue types, or between cells or tissues exposed to stress conditions, chemical compounds or pathogens, is critical to the understanding of mechanisms underlying various physiological conditions, disorders, or diseases. However, out of the many clones that are identified based on interesting expression patterns, only those representing known genes can be considered to be promising drugs or drug-targets. A significant portion of the differentially expressed, arrayed clones, are unknown ESTs frequently derived from untranslated cDNA regions or containing no informative structural protein patterns. Thus, no clues exist as to the potential function or sub-cellular localization of a large group of clones.

Since membranal and secreted proteins are both accessible and critical for transduction of numerous intra- and intercellular signals, they are generally viewed as preferred targets for pharmacological use and intervention. Therefore, the a priori classification of arrayed unknown gene sequences into those that potentially code for secreted and membranal proteins is of great value for the optimization of a high-throughput process of identifying potential drug targets. Furthermore, it would be useful to further identify additional genes which express membranal or secreted proteins that are differentially expressed in different, cellular situations is of the utmost importance in designing therapeutic or diagnostic tools.

SUMMARY OF THE INVENTION

The present invention provides a method of identifying clones which encode membranal and secreted proteins by preparing cell fractionations, preparing cDNA probes from template RNA derived from membrane-bound polysomes and free-polysomes, performing a microarray-based comparison of the relative abundance of different RNA species, analyzing the results and thereby identifying genes encoding for membranal and secreted proteins. Since membranal and secreted proteins are generally viewed as preferred targets for pharmacological intervention, the present invention thus provides a method of identifying likely targets for drug development. The present invention further provides a method of augmenting microarray analysis by utilizing RNA extracted from specific subcellular-compartments as templates for DNA probes.

DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1A:
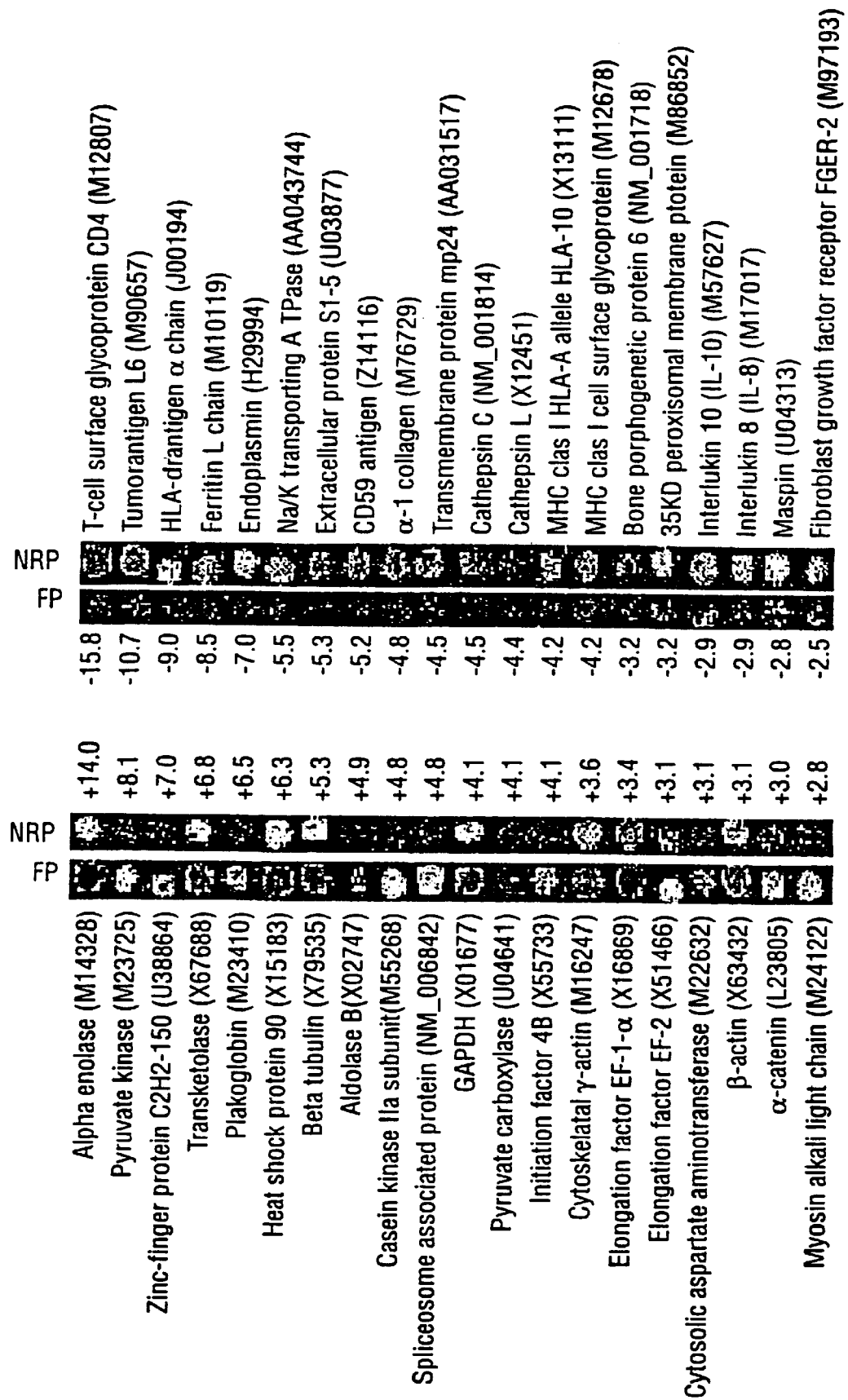
FIGS. 1A–C are graphs showing the distribution of RNA species and indifferent polysomal fractions depending on the subcelluar localization.

Generally, the present invention provides a method of detecting genes encoding for specific protein groups. More specifically, the present invention provides a microarray-based comparison of the relative abundance of different RNA species using cDNA probes derived from membrane-bound polysomes and free polysomes, for the purpose of identifying clones encoding for membranal or secreted proteins, and thereby identifying likely targets for drug development. The methodology of the present invention can easily be adapted to other gene technologies well known to those skilled in the art, that are used for the general detection of differentially expressed genes. As shown herein, microarray analysis can be augmented by utilizing RNA extracted from specific subcellular compartments as templates for cDNA probes, as described herein.

By the term "augmenting" according to the present invention it is meant that the microarray analysis is altered or changed. For example, augmenting includes but is not limited to, enabling the microarray analysis to function more sensitively and thus being able to detect the presence of additional RNAs.

The term "compartments" according to the present invention, refers to a fragment or portion of the cell. This includes but is not limited to free polysomes and membrane bound polysomes. Additional subcellular fragments may be utilized without departing from the spirit of the invention.

Compartments of RNA are derived by fractionation and lysis methods described below.

The term "microarray analysis" as used in the present invention, and particularly "DNA microarray analysis", is meant to include any means for determining the presence of specific RNA species in the RNA population derived from the various cellular compartments after their fractionation. Other modes of analysis which function similarly to those as set forth in the examples herein, can be used according to the methods of the present invention. Such other modes of analysis are well known to those skilled in the art.

DNA microarray analysis has become the major tool in the search for key genes involved in events underlying physiological and pathophysiological processes. Microarray-based comparison of the relative abundance of different RNA species using probes derived from membrane-bound polysomes and free, polysomes enables the identification of clones that potentially code for membranal and secreted proteins, thereby indicating preferred targets for drug development. This is achieved by comparison of transcript abundance in RNA fractions prepared from polysomes bound to rough endoplasmic reticulum and from polysomes located in the cytoplasm, allowing a reliable prediction of whether the gene of interest codes for a membranal or a secreted protein.

The source organism may be any organism which provides suitable mRNA. The mRNA sample is derived from cellular compartments based on protein localization which are differentially analyzed to identify genes regulated by a stress-inducing factor (U.S. Ser. No. 09/309,862 of same Applicant). This method is designed for identifying and cloning genes that code for membranal and secreted proteins. That is, the present method is designed for identifying and cloning genes which are preferred targets for drug development, namely membranal or secreted proteins.

As used herein, RNA refers to RNA isolated from cell cultures, cultured tissues or cells or tissues isolated from organisms which are stimulated, differentiated, exposed to a chemical compound, are infected with a pathogen or otherwise stimulated or from normal samples. RNA can be isolated from specific cellular compartments using a sucrose step analysis or by other suitable methods well known in the art. As used herein, translation is defined as the synthesis of protein on an mRNA template.

The method of the present invention synergistically integrates two types of previously known methodologies which were otherwise used separately. The first method is the division of cellular mRNA into separate pools of mRNA derived from different polysome pools. The second methodology involves the simultaneous comparison of the relative abundance of the mRNA species found in the separate pools by a method of differential analysis such as differential display (and its many variants), representational difference analysis (RDA), gene expression microarray (GEM), suppressive subtraction hybridization (SSH) (Diatchenko et al., 1996), and oligonucleotide chip techniques such as the chip technology exemplified by U.S. Pat. No. 5,545,531 to Rava et al. assigned to Affymax Technologies N.V. and direct sequencing exemplified by WO 96/17957 patent application to Hyseq, Inc.

Briefly, subtractive hybridization is defined as subtraction of mRNA by hybridization in solution. RNAs that are common to the two pools form a duplex that can be removed, enriching for RNAs that are unique or more abundant in one pool. Differential Display is defined as reverse transcription of mRNA into cDNA and PCR amplification with degenerated primers. Comparison of the amounts amplification products (by electrophoresis) from two pools indicate transcript abundance. RDA, GEM, SSH, SAGE are described herein above.

The specific cells/tissues which are to be analyzed in order to identify translationally regulated genes, can include any suitable cells and/or tissues. Any cell type or tissue can be used, whether an established cell line or culture or whether directly isolated from an exposed organism.

The fractionation can be completed to create polysomal subdivisions. The subdivisions can be made to discriminate between total polyribosomes or membrane-bound ribosomes by methods known in the art (Mechler, 1987). These subdivisions can be created using a sucrose step gradient. More specifically, a cell lysate can be prepared using a TEA based hypotonic buffer, which can then be analyzed for mRNA intactness using RNAse inhibitors. Then rough endoplasmic reticulum is separated from other cytoplasmic components using a sucrose step gradient.

Microsomal fractions may be obtained using the methods of the present invention as set forth in the Experimental Section which are modifications of the methods disclosed by Walter and Blobel in 1983.

Following isolation and division of the total mRNA population into separate protein localization pools of mRNA, the relative abundance of the many mRNA species found in these pools are simultaneously compared using a differential analysis technique such as differential display, oligonucleotide chips, representational difference analysis (RDA), GEM-Gene Expression Microarrays (Schena et al., 1995, Aiello et al., 1994, Shen et al., 1995, Bauer et al., 1993, Liang and Pardee, 1992, Liang and Pardee, 1995, Liang et al., 1993, Braun et al., 1995, Hubank and Schatz, 1994) and suppressive subtraction hybridization (SSH). The RNA isolated from the fractions can be further purified into mRNA without the ribosomal RNA by poly A selection. It should be noted that multiple pools can be analyzed utilizing this method. That is, different cell aliquots subjected to different stressors can be compared with each other as well as with the reference sample.

Labeled nucleic acid probes.(in a cDNA PCR product or rRNA transcribed from the cDNA) made from RNA derived from polysomal pools can be used as probes to identify clones of cDNA, oligonucleotides, genomic clones, and mRNA species that are fixed onto a solid matrix-like microarrays such as GEM (shown in U.S. Pat. No. 5,545,531 to Rava et al. and WO96/17957 to Hyseq, Inc.), and membranes of any kind where clones can be either blotted after electrophoresis or directly loaded (dot blot) onto the membrane. The label can be radioactive, fluorescent, or incorporating a modified base such as digoxigenin and biotin.

The above discussion provides a factual basis for the use of the identification methods of the present invention. The methods used with and the utility of the present invention can be shown by the non-limiting examples and accompanying figures included herein.

METHODS

General Methods

General methods in molecular biology: Standard molecular biology techniques known in the art and not specifically described were generally followed as in Sambrook et al., *Molecular Cloning: A Laboratory Manual*, Cold Spring Harbor Laboratory Press, New York (1989), and in Ausubel et al., *Current Protocols in Molecular Biology*, John Wiley and Sons, Baltimore, Md. (1989) and in Perbal, *A Practical Guide to Molecular Cloning*, John Wiley & Sons, New York (1988), and in Watson et al., *Recombinant DNA*, Scientific American Books, New York and in Birren et al (eds) *Genome Analysis: A Laboratory Manual Series, Vols.* 1–4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in *PCR Protocols: A Guide To Methods And Applications*, Academic Press, San Diego, Calif. (1990). In-situ (In-cell) PCR in combination with Flow Cytometry can be used for detection of cells containing specific DNA and mRNA sequences (Testoni et al, 1996, Blood 87:3822.)

General methods in immunology: Standard methods in immunology known in the art and not specifically described are generally followed as in Stites et al.(eds), Basic and Clinical Immunology (8th Edition), Appleton & Lange, Norwalk, Conn. (1994) and Mishell and Shiigi (eds), Selected Methods in Cellular Immunology, W. H. Freeman and Co., New York (1980).

Immunoassays

In general, ELISAs are the preferred immunoassays employed to assess a specimen. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, *Molecular Cloning: A Laboratory Manual*, Cold Springs Harbor, N.Y., 1989.

Experimental Protocols

Cell culture protocols.

Hela and Jurkat cell lines (ATCC) were grown either in DMEM (HeLa) or in RPMI (Jurkat) supplemented with 10% FCS. HeLa and Jurkat cells were kept under normal tissue culture conditions. One to three hours prior to harvesting (for non-treated cells) or prior to treatment, culture medium was replaced with a fresh one. Cells were then washed with ice cold PBS-/-, harvested on ice and either directly processed to extraction of total RNA or collected by centrifugation (400 g, 5 minutes). The cell pellet was immediately frozen in liquid nitrogen and kept at –70° C. until used for fractionation to isolate nuclei, polysomes or microsomes.

Preparation of membrane bound and free polysomes. For isolation of microsomes, Hela cells were grown to 50%–70% confluence and Jurkat cells were grown to cell densities $0.5-1 \times 10^6$ cells/ml. Cytoplasmic lysate was prepared essentially as described (Walter and Blobel, 1983). Briefly, Hela or Jurkat cell pellets were thawed on ice and lysed with 0.25M sucrose lysis buffer (250 mM sucrose, 50 mM TEA (triethanolamine), 50 mM KOAc pH 7.5, 6 mM Mg(OAc)2, 1 mM EDTA, 1 mM DTT, 0.5 mM PMSF, 200 units/ml RNasine (Promega), 0.1 mg/ml heparin)—1 ml per $10^8$ cells. Cells were homogenized on ice using a Teflon homogenizer (Heidolph, 1000 rpm). Following centrifugation (600 g, 10 minutes, 4° C.), the supernatant was collected and kept on ice. The nuclei pellet was washed with 1 ml of lysis buffer and re-centrifuged (600 g, 10 minutes, 4° C.) to release the contaminating microsomes. The resultant supernatant was combined with the previous one. Total supernatant material was further centrifuged to precipitate mitochondria (10000 g, 10 minutes, 4° C.) and heparin (1 mg/ml) was added to the collected supernatant. The latter (5 ml) was layered over the two-step sucrose gradient (2.5 ml of 2.05M sucrose in lysis buffer/2.5 ml of 1.5M sucrose in lysis buffer). After centrifugation (100,000 g, 3 hours, 4° C.), the upper phase (5 ml) containing mRNPs was discarded. Middle phase (2.5 ml) containing membrane bound polysomes (MBP) and pellet containing free polysomes (FP) were further used for RNA extraction.

Extraction of RNA from membrane bound (MBP) and free polysomes (FP). Pellet of free polysomes was dissolved in 1% SDS/0.1M NaCl. Membrane polysome fraction was diluted with TE 1:1 and SDS and proteinase K (Sigma) were added to final concentrations 1% and 0.1 mg/ml, respectively. Following incubation at 37° C. for 30 minutes, RNA was purified from both fractions with phenol:chloroform (1:1) and precipitated with 0.3M NaOAc, 20 µg/ml glycogen (Roche) and 50% isopropanol. Following centrifugation (10,000 g, 20 minutes, 4° C.), RNA pellets were washed with 70% ethanol, dried and dissolved in $H_2O$.

Human UniGEM1 microaffay (Incyte). This commercially available microarray that contains 9,700 human cDNA clones, 60% of them coding for known genes, was used in experiments with MBP and FP derived probes. Since proper interpretation of experimental data requires precise clone identity, only clones that were verified by sequencing in Incyte (2,800 out of 9,700) were subjected to the analysis.

Probe Labeling and Hybridization to cDNA Microarrays cDNA probes were synthesized from 50 µg of RNA using reverse transcriptase (Superscript, Gibco-BRL) and 18-mer oligo-dT primer. The hybridization probe was composed of two cDNA populations, derived from two different RNA sources: one labelled with Cy3-dCTP and the other with Cy5-dCTP (Amersham), as previously described (Schena et al., 1996). The following types of probes were used for hybridizations to different DNA microarrays:

Unigem1(Incyte). This microarray was utilized for hybridization of probes derived from different polysomal fractions: (1) MBP RNA from Hela (Cy3)/FP RNA from Hela (Cy5); (2) MBP RNA from Jurkat (Cy3)/FP RNA from Jurkat (Cy5).

Hybridization Data Processing

Hybridizations, image processing and signal calculation were performed using commercial tools (Incyte, GEMTools). Overall signals were balanced by this software and differential expression values were calculated as "Cy3 signal" (P1)/"balanced Cy5 signal" (P2) (P2>P2) and "balanced Cy5 signal" (P2)/"Cy3 signal" (P1) (P2>P1). For this reason, the numerical values shown in the tables a may vary from the observed images. For all differentially expressed clones the image data was visually inspected. Since there was observed a certain inconsistency of hybridization results obtained with low expressed cDNA clones, in all experiments only clones that displayed an hybridization signal not lower than 500 units, at least in one of the fluorescence channels, were subjected to further analysis.

Analysis of Discrimination of MBP and FP cDNA Populations

Out of the annotated expressed clones, a random sample of 118 clones was selected and the subcellular localization of their encoded proteins was assigned. According to the literature and the SWISS-PROT database (Bairoch and Apweiler, 2000), 29 of them code for either membranal/secreted or ribosomal proteins (MBP-resident), 63 code for cytosolic or nuclear proteins (FP-resident), and the remaining 26 genes could not be clearly assigned. Frequency histograms were built for In(P1signal/P2 Balanced Signal) since these values are anticipated to be approximated well by a normal distribution (while differential expression values are not). The parameters of normal distributions were then estimated for each histogram according to standard procedures, using the SPSS package, which was also used for the standard statistical tests for inequality of means of the approximated normal distributions (t-test).

Determination of Conditional Probabilities for cDNA Clones to Correspond to the Membranal/Secreted or to the Cytosolic/Nuclear Group of Proteins In order to calculate the conditional probabilities, the a priori probability was first estimated for a selected clone to be MBP-resident ($\alpha 1$ in equations (1,2)). This estimation is required since the relative portions of the two clone populations both on the array and in the expressed RNA population are probably not equal (more cytosolic/nuclear clones are expected), thereby biasing in advance their probability of detection. This a priori probability for a protein to be MBP-resident ($\alpha 1=0.34$, equation (1)) was calculated based on the assignment of proteins with prominent differential values >0.69 (right tail, corresponding to >+2 differential expression values) and <−0.69 (left tail, corresponding to <−2 differential expression values) of the distribution, as given in Table 2, so that a combined distribution would have these pre-determined right and left tail frequencies. The parameter al was found as a solution of the equation:

$$FL1 + FR1 = \frac{a1?\left(1 - \Phi\left(\frac{w-m1}{SD1}\right)\right)}{a1?\left(1 - \Phi\left(\frac{w-m1}{SD1}\right)\right) + (1-a1)?\left(1 - \Phi\left(\frac{w-m2}{SD2}\right)\right)} + \frac{a1?\Phi\left(\frac{-w-m1}{SD1}\right)}{a1?\Phi\left(\frac{-w-m1}{SD1}\right) + (1-a1)?\Phi\left(\frac{-w-m2}{SD2}\right)} \quad (1)$$

where w=0.69, m1,m2 means of the two distributions, SD1, SD2 —their standard deviations, $\Phi$ is standard normal distribution function (i.e.

$$\Phi(y) = \frac{1}{\sqrt{2\pi}} \int_{-x}^{y} \exp\left(-\frac{x^2}{2}\right) dx),$$

FL1 (FR1)—the frequency of first kind (MBP-resident) proteins to have prominent differential values less than −w (more than w), FL2 (FR2)—the frequency of second kind (FP-resident) proteins to have prominent differential values less than −w (more than w).

The conditional probabilities for proteins of the first kind (encoded by the MBP-resident mRNAs) and second kind (encoded by the FP-resident mRNAs) (p1 and p2, respectively) under assumption on normality of distributions were calculated according to the following equation:

$$p1(w) = \frac{a1?\exp\left(-\frac{(w-m1)^2}{2(SD1)^2}\right)}{a1?\exp\left(-\frac{(w-m1)^2}{2(SD1)^2}\right) + (1-a1)?\exp\left(-\frac{(w-m2)^2}{2(SD2)^2}\right)} \quad (2)$$

where w=In(P1signal/P2BalancedSignal) and $\alpha 1$ is the a priori probability for a protein to be of the first kind.

Bioinformatics Sequence Analysis of Selected EST Clones

The EST sequences were extended using QBI's propriety clustering software (manuscript in preparation). Putative coding regions for the obtained contig sequences were defined by two criteria: (1) open reading frame (ORF) longer than 50 amino acids, flanked by untranslated region(s) containing multiple stop codons in all three frames; and (2) when a potential 5' UTR was observed, the presence of an initiation methionine was required; (it was sometimes possible to define it relative to the poly-A tail). The contigs were characterized in two steps. First, homology searches (BLAST) were performed to identify homologous sequences in the nucleotide and protein non-redundant (nr) databases of Genbank. Then the contig sequences were characterized by prediction of motifs and domains using SMART (Schultz et al., 1998), prediction of intracellular localization using PSORT (Nakai and Kanehisa, 1992), searching for homologous domains in the ProDom database (Corpet et al., 1999), and searching for homologous motifs in ProSite database (Hoffmann et al., 1999).

RESULTS AND DISCUSSION

Assessment of Subcellular Localization of Putative Proteins by Application of Probes Derived from RNA Extracted from Different Polysomal Sub-fractions.

In order to elucidate the molecular mechanisms underlying physiological and pathological conditions, global gene expression profiles should be deconstructed and specific genes of interest identified. Among these, secreted and membranal proteins are natural prime targets both for drug development and for the investigation of physiological phenomena. This is due to the key role they play in initiating and orchestrating complex responses as well as to their accessibility for manipulation.

It is well established that secreted and membranal proteins are synthesized by polysomes located on the rough endoplasmic reticulum (membrane-bound polysomes—MBP) (Mechler, B. M., 1987; Rapoport, 1992). Membrane-associated synthesis differentiates these proteins (and the mRNAs that encode them) from other intracellular proteins that are synthesized on cytoplasmic free polysomes (FP). Differential profiling of mRNA extracted from these two distinct fractions, MBP and FP, can indicate mRNAs that are over-represented in one fraction over the other, and, therefore, would enable us to assign putative protein sub-cellular localization according to the polysomal localization of the corresponding mRNAs.

EXAMPLE 1

The ability to discriminate between membranal/secreted and other proteins based on the assignment of their corresponding mRNAs was tested in two cell systems: a cervical carcinoma cell line (HeLa) and a T-cell lymphoma line (Jurkat). In each case RNA was prepared from isolated MBP and FP fractions, and cDNA probes were produced and hybridized to the generic human UniGEM1 cDNA microarray. Nearly 60% (HeLa) or 47% (Jurkat) of the clones on the array gave a hybridization signal. Indeed, when examining strongly differential clones (over 2-fold difference between MBP and FP) for which sub-cellular localization of the corresponding proteins is already known, a clear correspondence emerges between differential expression and protein localization (Table 1).

HeLa-specific probes have identified 91 clones displaying a higher hybridization signal with MBP RNA (two fold or more difference). An illustrative portion of the hybridization image is shown in FIG. 1A. The Jurkat-specific probe revealed 50 clones with similar characteristics. In both cell systems, approximately 60% of clones which were at least 2-fold over-represented in the MBP RNA fraction (differential value<=−2) coded for known secreted, membranal or RER-resident proteins. These include secreted proteins like thrombospondin 1, interleukins, transmembrane receptors such as thrombin receptor, FGF2 receptor, TRAMP and others; and integral rough endoplasmic reticulum proteins such as ribophorin II, reticulocalbin and signal recognition particle 19 kd. In addition, all ribosomal proteins were invariably identified within the MBP fraction. In the past, it has been suggested that ribosomal proteins are synthesized on "loosely" bound polysomes (Hovland et al., 1995) and are, therefore, theoretically legitimate for preferential detection by the MBP probe.

To summarize, 75% of the clones over-represented in the MBP fraction (including those coding for ribosomal proteins), indeed belong to the expected protein classes. Furthermore, 95% of clones which were represented at least 2-fold more in the FP fraction (differential value>=2) coded for cytosolic or nuclear proteins (Table 1). In both cases there was observed a minor and currently unexplainable contamination (4%–6%) with clones corresponding to RNA species translated within mitochondria. Thus, significant differences in RNA abundance between membrane-bound and free polysomes seem to distinguish between clones coding for sercreted/membranal and cytosolic/nuclear proteins, albeit to different extents.

Significantly, all clones that appeared to be wrongly assigned were only sporadically detected in one cell-line, but not in both. The hybridization profile of 309 clones that gave hybridization signal in both Jurkat and HeLa cells was well correlated (r=0.86401), indicating a consistent distribution of identical mRNAs between the two polysomal fractions regardless of their cell source. An even better correlation was observed between two independent experiments with the same cell type (r=0.91478).

EXAMPLE 2

Figure 1B:
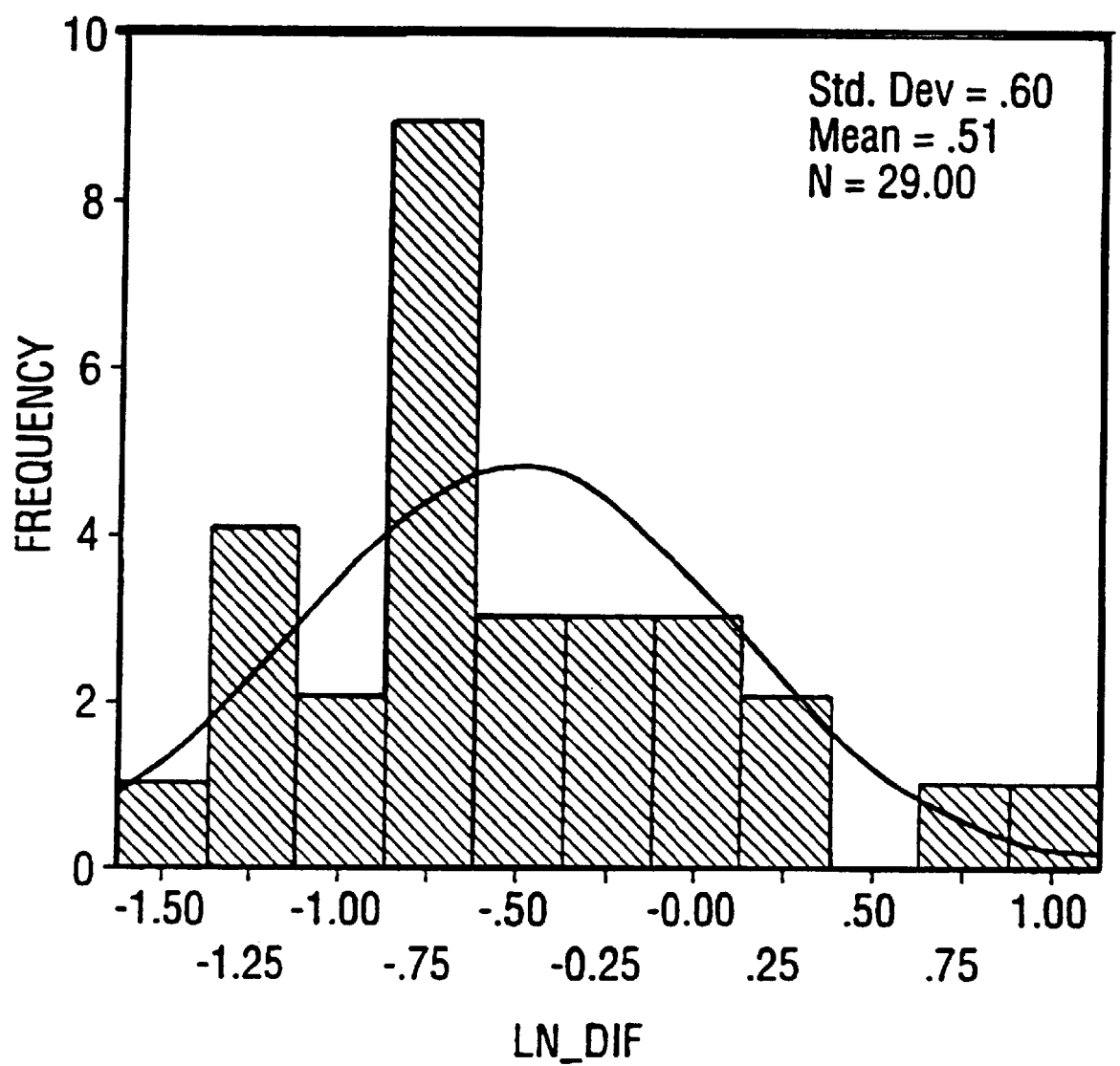
Figure 1C:
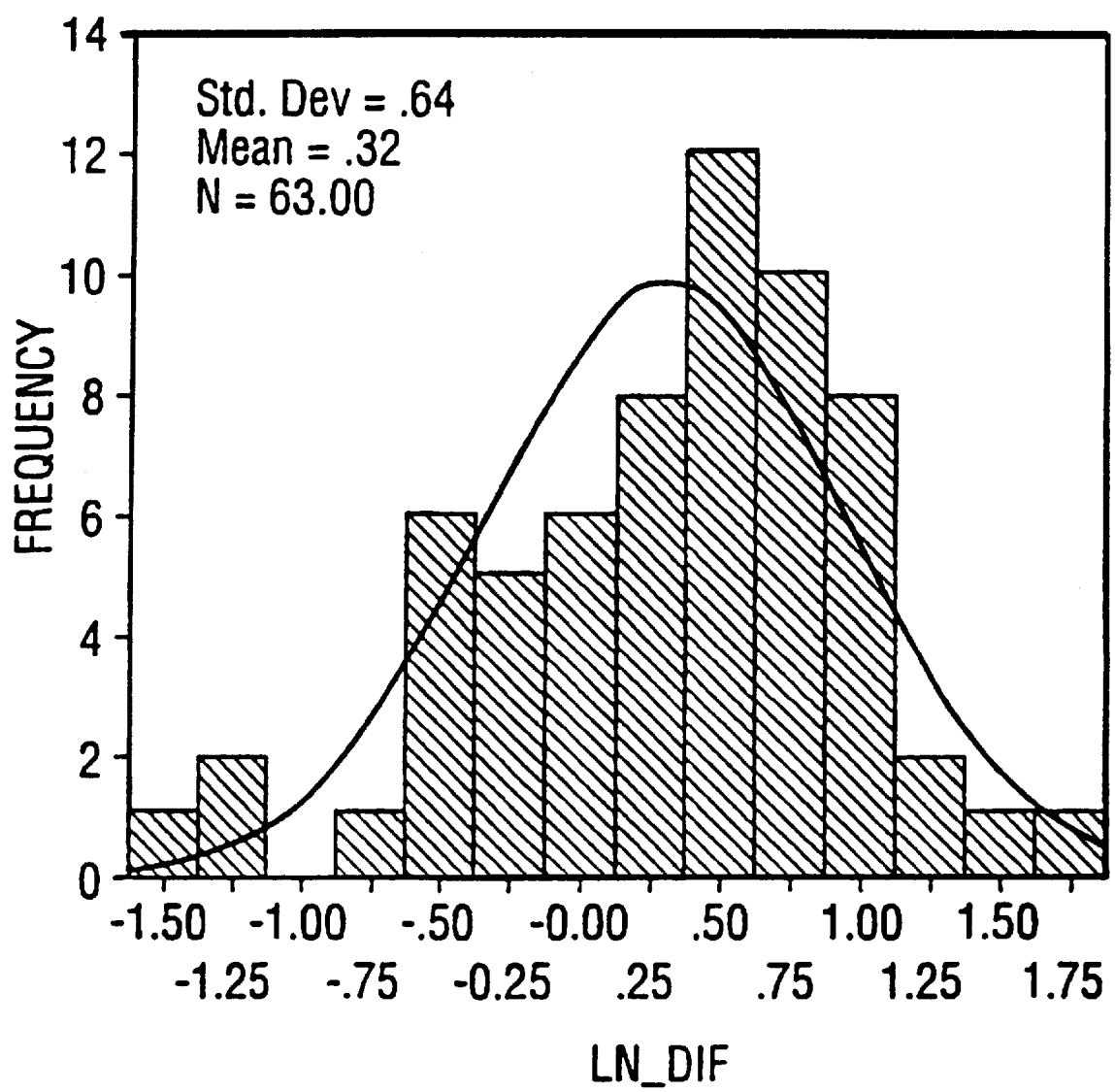

To further support the validity of the differential profiling method, and in order to establish reliable thresholds, the expression profiles from the HeLa cell system were statistically analyzed. First, the discriminative power of the method was evaluated by comparing the differential expression distributions obtained for randomly selected and pre-annotated populations of clones: one for MBP-resident and one for FP-resident transcripts. For each of the two assigned populations, a frequency histogram of log-transformed expression values was built (FIG. 1B and C), and a normal distribution was approximated. The clear difference between the means of these two distributions (m1=−0.51, SD1=0.6 and m2=0.32, SD2=0.64) was significant (t-test 5.89; DF=90; p<0.0001). Thus, the expression profiles do indeed correspond to two distinct populations of transcripts, supporting the discriminative nature of the proposed method.

The clear differences in the two distributions made it possible to further determine thresholds for reliable assignment of sub-cellular localization of putative proteins based on the relative abundance of corresponding RNAs in the MBP and FP fractions. To this end, two conditional probabilities were calculated: the probabilities for a -clone with a given differential expression value (between MBP and FP probes) to be truly MBP-resident or FP-resident (eqn (2) in the Experimental Protocols). The calculated probabilities allowed us to set a selective differential value threshold for a required level of accuracy (see table of calculated probabilities. For example, for a clone with a differential expression value +2 (+2.5) or higher, the probability of being indeed FP-resident (cytosolic or nuclear) is over 92% (95%), while for a clone with a differential expression value −2.4 (−3.1) or lower, the probability of indeed being MBP-resident (membranal, secreted or ribosomal) is over 70% (80%).

Thus, both qualitative and quantitative evaluation of the data indicates the validity and reliability of this straightforward predictive method. Importantly, the thresholds calculated by thorough analysis indicate that for the process of detection of secreted and membranal proteins the method will present a very low false negative rate, and a reasonable false positive rate. Since most wrongly assigned clones do not seem to be repeatedly detected in separate experiments, their occurrence is probably due to technical problems in extraction procedures. Such problems may be overcome by repetition of experiments and by improvement of the technology. Other, more consistent "errors" that are probably biologically meaningful, such as the detection of ribosomal and mitochondrial proteins as synthesized on MBP, can usually be filtered out on the basis of sequence information.

EXAMPLE 3

The significance of the approach for gene discovery was further illustrated by the detection of genes potentially coding for novel and known membranal proteins from among the EST clones with differential expression values that reliably indicate an MBP-resident transcript. 12 EST clones that had not been previously annotated by Incyte (Table 2) were selected. The EST sequences were extended using proprietary clustering and contig assembly software (manuscript in preparation), producing contigs which were on average 3-fold longer than the original EST sequences (Table 2). The contigs were characterized by sequence and motif homology searches (as detailed in Experimental Protocols). Three out of the 12 contigs included a significant ORF. In all three cases, sequence homology, protein motifs and sorting signals indicate that these are indeed membranal proteins (Table 2): (1) clone 322080 was found to be the SERP1 gene (AB022427) a human orthologue of the rat ribosome associated membrane protein RAMP4 (AJ238236) (Schroder et al., 1999). (2) the contig for clone 485173, which was found to possess a putative coding sequence of 235 amino acids, was predicted to have a signal peptide and four transmembrane domains; (3) a similar prediction for a membranal status was made for the 160 amino acid ORF identified within the contig from clone 429959. Moreover, the predicted protein was found to be homologous to a lysosomal-associated multispanning membrane protein (U51240) (Adra et al., 1996). These findings further underscore the importance of the proposed approach.

Several screening methods that have emerged to facilitate identification of novel secreted and membranal proteins. However, all of them are laborious and involve an expression-cloning step based on the utilization of known structural features, the presence of signal peptide or transmembrane domain(s) (Chen et al., 1996; Tashiro et al, 1993). The method of the invention, which is independent of the availability of open reading frame information and relies solely on cell fractionation and RNA isolation procedures, significantly extends the utility of microarray applications by allowing the rapid identification of highly relevant membranal and secreted proteins.

The technological improvements of cDNA microarray analysis presented herein clearly and reliably extend and augment expression-based gene discovery. They allow comprehensive measurement of gene expression embracing various modes of gene regulation as well as a high-throughput sequence-independent classification of arrayed clones according to the sub-cellular localization of encoded proteins. This greatly increases the scope of microarray analysis and optimizes the process of selection of potential pharmacological targets.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Adra, C. N. et al. LAPTM5: a novel lysosomal-associated multispanning membrane protein preferentially expressed in hematopoietic cells. *Genomics* 35, 328–337 (1996).

Aiello et al, 1994 [see p.7—COMPLETE]

Ausubel [see p. 8—COMPLETE]

Bairoch, A. & Apweiler, R. The SWISS-PROT protein sequence database and its Schultz, J., Milpetz, F., Bork, P. & Ponting, C. P. SMART, a simple modular architecture research tool: identification of signaling domains. *Proc Nati Acad Sci U.S.A.* 95, 5857–5864 (1998).supplement TrEMBL in 2000. *Nucleic Acids Res* 28, 45–48 (2000).

Bassett, D. E., Jr., Eisen, M. B. & Boguski, M. S. Gene expression informatics—it's all in your mine. *Nat Genet* 21, 51–55 (1999).

Bauer et al., 1993 [see p.7—COMPLETE]

Birren et al., [see p. 8—COMPLETE]

Braun et al, 1995[(see p. 7—COMPLETE]

Chen, S. L. et al. Isolation and characterization of a novel gene expressed in multiple cancers. *Oncogene* 12, 741–751 (1996).

Corpet, F., Gouzy, J. & Kahn, D . Recent improvements of the ProDom database of protein domain families. *Nucleic Acids Res* 27, 263–267 (1999).

Diatchenko et al., 1996 [see p. 67 —COMPLETE]

Eisen, M. B., Spellman, P. T., Brown, P. O. & Botstein, D. Cluster analysis and display of genome-wide expression patterns. *Proc Natl Acad Sci U.S.A.* 95, 14863–14868 (1998).

Feng, Y. et al Transcriptional Profile of Mechanically Induced Genes in Human Vascular Smooth Muscle Cells. *Circ Res* 85,1118–1123 (1999).

Hofmnann, K., Bucher, P., Falquet, L. & Bairoch, A. The PROSITE database, its status in 1999. *Nucleic Acids Res* 27, 215–219 (1999).

Hovland et al., The mRNAs for cyclin A, c-myc and ribosomal proteins L4 and S6 are associated with cytoskeletal-bound polysomes in HepG2 cells. *Biochem J.* 310, 193–196 (1995).

Hubank and Schatz, 1994 [see p. 8—COMPLETE]lyer, V. R. et al. The transcriptional program in the response of human fibroblasts to serum [see comments]. *Science* 283, 83–87 (1999).

Liang & Pardee, 1992, [see p. 7—COMPLETE]

Liang & Pardee, 1995, [see p. 7—COMPLETE]

Liang et al, 1993 [see p. 7—COMPLETE]

Mechler, B. M. Isolation of messenger RNA from membrane-bound polysomes. *Methods Enzymol* 152, 241–248 (1987).

Mishel and Shiigi [see p. 9 —COMPLETE]

Nakai, K. & Kanehisa, M. A knowledge base for predicting protein localization sites in eukaryotic cells. *Genomics* 14, 897–911 (1992).

Perbal [see p. 8—COMPLETE]

Rapoport, T. A. Transport of proteins across the endoplasmic reticulum membrane. *Science* 258, 931–936 (1992).

Sambrook et al [see p. 8—COMPLETE]

Schena, M. et al., Parallel human genome analysis: microarray-based expression monitoring of 1000 genes. *Proc Natl Acad Sci U.S.A.* 93, 10614–10619 (1996).

Schroder, K. et al. Control of glycosylation of MHC class II-associated invariant chain by translocon-associated RAMP4. *Embo J* 18, 4804–4815 (1999).

Shen et al., 1995 [see p. 7—COMPLETE]

Spellman, P. T. et al. Comprehensive identification of cell cycle-regulated genes of the yeast *Saccharomyces cerevisiae* by microarray hybridization. *Mol Biol Cell* 9, 3273–3297 (1998).

Stites et al., 1994 [see p. 9—COMPLETE]Tashiro, K. et al Signal sequence trap: a cloning strategy for secreted proteins and type I membrane proteins. *Science* 261, 600–603 (1993).

Testoni et al, 1996 [see p. 8—COMPLETE]

Walter, P. & Blobel, G. Signal recognition particle: a ribonucleoprotein required for cotranslational translocation of proteins, isolation and properties. *Method Enzymol* 96, 682–691 (1983).

Wang, K. et al. Monitoring gene expression profile changes in ovarian carcinomas using cDNA microarray. *Gene* 229, 101–108 (1999).

Watson [see p. 8—COMPLETE]

Whitney, L. W. et al. Analysis of gene expression in mutiple sclerosis lesions using cDNA microarrays. *Ann Neurol* 46, 425–428 (1999).

What is claimed is:

1. A method of identifying clones obtained from a cell type or tissue which encode membranal or secreted proteins, comprising the steps of:

a) preparing cell fractionations obtained from the cell type or tissue;

b) isolating membrane bound polysomes and free polysomes from the cell fractionations;

c) extracting intact total RNA from membrane bound polysomes and free polysomes, respectively;

d) preparing cDNA probes from template RNA derived from the respective extracted polysomes;

e) hybridizing cDNA probes to a DNA microarray;

f) performing microarray-based comparison of the relative abundance of the different RNA species;

g) analyzing the results according to conditional probabilities; and h) identifying genes or clones encoding membranal or secreted proteins.

2. The method according to claim 1, wherein the membrane bound polysomes and free polysomes are isolated from the cell fractionations by sucrose step analysis.

3. The method according to claim 1 wherein the genes or clones encoding membranal or secreted proteins identify likely targets for drug development.

4. The method according to claim 1, wherein the membrane bound polysomes are obtained from rough endoplasmic reticulum membranes.

5. The method according to claim 1, wherein the cell type or tissue is obtained from an established cell line, from a culture, or directly isolated from an exposed organism.

* * * * *